United States Patent
Capoglu et al.

(10) Patent No.: US 10,544,671 B2
(45) Date of Patent: Jan. 28, 2020

(54) AUTOMATED INVERSION WORKFLOW FOR DEFECT DETECTION TOOLS

(71) Applicant: Halliburton Energy Services, Inc., Houston, TX (US)

(72) Inventors: Ilker R. Capoglu, Houston, TX (US); Burkay Donderici, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/758,858

(22) PCT Filed: Nov. 6, 2016

(86) PCT No.: PCT/US2016/060751
§ 371 (c)(1),
(2) Date: Mar. 9, 2018

(87) PCT Pub. No.: WO2018/084863
PCT Pub. Date: May 11, 2018

(65) Prior Publication Data
US 2019/0032480 A1  Jan. 31, 2019

(51) Int. Cl.
*E21B 47/10* (2012.01)
*G01N 17/02* (2006.01)
(Continued)

(52) U.S. Cl.
CPC ........ *E21B 47/1025* (2013.01); *E21B 47/082* (2013.01); *E21B 47/09* (2013.01); *E21B 47/124* (2013.01); *G01N 17/02* (2013.01)

(58) Field of Classification Search
CPC .... E21B 47/1025; E21B 47/082; E21B 47/09; E21B 47/124; G01N 17/02; G01N 27/90
See application file for complete search history.

(56) References Cited

U.S. PATENT DOCUMENTS

| | | | |
|---|---|---|---|
| 6,483,777 B1 | 11/2002 | Zeroug | |
| 7,095,223 B2 * | 8/2006 | Yoo | E21B 47/0905 324/221 |

(Continued)

FOREIGN PATENT DOCUMENTS

| | | |
|---|---|---|
| WO | 2013162505 | 10/2013 |
| WO | 2015024690 | 2/2015 |

(Continued)

OTHER PUBLICATIONS

International Search Report and Written Opinion for Application No. PCT/US2016/060751 dated Jul. 21, 2017.
(Continued)

*Primary Examiner* — Yong-Suk Ro
(74) *Attorney, Agent, or Firm* — Benjamin Fite; C. Tumey Law Group PLLC

(57) ABSTRACT

A methods for the detection of pipe characteristics. The method may comprise disposing a defect detection tool in a wellbore, processing measurements from the defect detection tool in the wellbore to obtain a well log, storing the well log in a database, importing the well log from the database into inversion software, loading a well plan into the inversion software, determining collar locations on at least one concentric pipe in the wellbore utilizing a collar locator algorithm in the inversion software using the well log and well plan, calibrating a forward model in the inversion algorithm utilizing a calibration algorithm in the inversion software, generating an output log utilizing the inversion algorithm in the inversion software on the inversion zone, and determining false metal loss in the output log using the output log.

18 Claims, 4 Drawing Sheets

(51) Int. Cl.
  *E21B 47/08*  (2012.01)
  *E21B 47/09*  (2012.01)
  *E21B 47/12*  (2012.01)

(56) References Cited

U.S. PATENT DOCUMENTS

| | | |
|---|---|---|
| 7,795,864 B2 | 9/2010 | Barolak et al. |
| 2003/0076107 A1 | 4/2003 | Fanini et al. |
| 2008/0276731 A1* | 11/2008 | Fagbayi .................. C23F 13/04 73/865.8 |
| 2012/0308174 A1 | 12/2012 | Head |
| 2014/0216734 A1 | 8/2014 | Hupp |
| 2015/0308980 A1* | 10/2015 | Bittar .................... E21B 47/082 73/152.54 |
| 2016/0070018 A1 | 3/2016 | Nichols et al. |
| 2016/0194948 A1 | 7/2016 | Donderici et al. |

FOREIGN PATENT DOCUMENTS

| | | |
|---|---|---|
| WO | 2016007267 | 1/2016 |
| WO | 2016007894 | 1/2016 |
| WO | 2016010917 | 1/2016 |
| WO | 2018031036 | 2/2018 |

OTHER PUBLICATIONS

"Fundamental Analysis of the Remote-Field Eddy-Current Effect" by Haugland published in IEEE Transactions on Magnetics vol. 32, No. 4 in Jul. 1996.

* cited by examiner

AUTOMATED INVERSION WORKFLOW FOR DEFECT DETECTION TOOLS

BACKGROUND

For oil and gas exploration and production, a network of wells, installations and other conduits may be established by connecting sections of metal pipe together. For example, a well installation may be completed, in part, by lowering multiple sections of metal pipe (i.e., a casing string) into a borehole, and cementing the casing string in place. In some well installations, multiple casing strings are employed (e.g., a concentric multi-string arrangement) to allow for different operations related to well completion, production, or enhanced oil recovery (EOR) options.

Corrosion of metal pipes is an ongoing issue. Efforts to mitigate corrosion include use of corrosion-resistant alloys, coatings, treatments, and corrosion transfer, among others. Also, efforts to improve corrosion monitoring are ongoing. For downhole casing strings, various types of corrosion monitoring tools are available. One type of corrosion detection tool uses electromagnetic (EM) fields to estimate pipe thickness or other corrosion indicators. As an example, an EM logging tool may collect EM log data, where the EM log data may be interpreted to correlate a level of flux leakage or EM induction with corrosion. When multiple casing strings are employed together, correctly managing corrosion detection EM logging tool operations and data interpretation may be complex.

BRIEF DESCRIPTION OF THE DRAWINGS

These drawings illustrate certain aspects of some examples of the present disclosure, and should not be used to limit or define the disclosure.

DETAILED DESCRIPTION

This disclosure may generally relate to methods for detection of pipe characteristics, such as defect detection, including corrosion inspection, of downhole tubulars and overall thickness estimation of downhole tubulars (e.g., pipes such as casing and/or production tubing). More specifically, this disclosure may relate to techniques that may aid in the automation of electromagnetics-based casing corrosion inspection. The corrosion inspection may be done by collecting electromagnetic data using a cased-hole tool, and subsequently processing the electromagnetic data in a post-processing inversion algorithm. The output of the inversion algorithm may be the metal loss in a number of concentric metallic tubulars. This disclosure may relate to a workflow for the entire post processing procedure, wherein steps can be automated and carried out with limited human interaction. This may lead to maximum efficiency and speed, which may be crucial in the current market where inspection results may be required within a matter of hours. Electromagnetic casing corrosion inspection may be performed by two techniques: an eddy-current technique and the magnetic flux leakage technique. The workflow described in this disclosure may be primarily applicable to the eddy-current technique, although it may be applicable to the magnetic flux leakage technique by certain modifications.

The present disclosure may include one or more of the following: Automatic Ghost Removal: feeding the casing collar detection outputs to a ghost removal algorithm; Iterative Adjustments: using results from a first iteration to adjust well plan information, casing collar locations, ghost locations and inversion weights; Override Flexibility: an ability to use alternate manual inputs for unreliable information (e.g., well plan, casing collar locations); Advanced Quality Control: an ability to visualize calibration coefficients, match between total thickness from individual pipes and RFEC, and adjust inversion parameters accordingly; Pipe or Zone Based Customization: an ability to vary algorithm specific parameters for each pipe or zone; Processing Workflow: a specific order of processing steps in relation to one another: i) calibration being performed based on weight assignments, ii) inversion being executed after calibration, iii) weight assignment, collar detection and ghost detection being applied after an inversion; Computational Time Control: an ability to switch between fast and slow inversion in different sections and distribute the inversion to multiple computers using various schemes.

Figure 1:
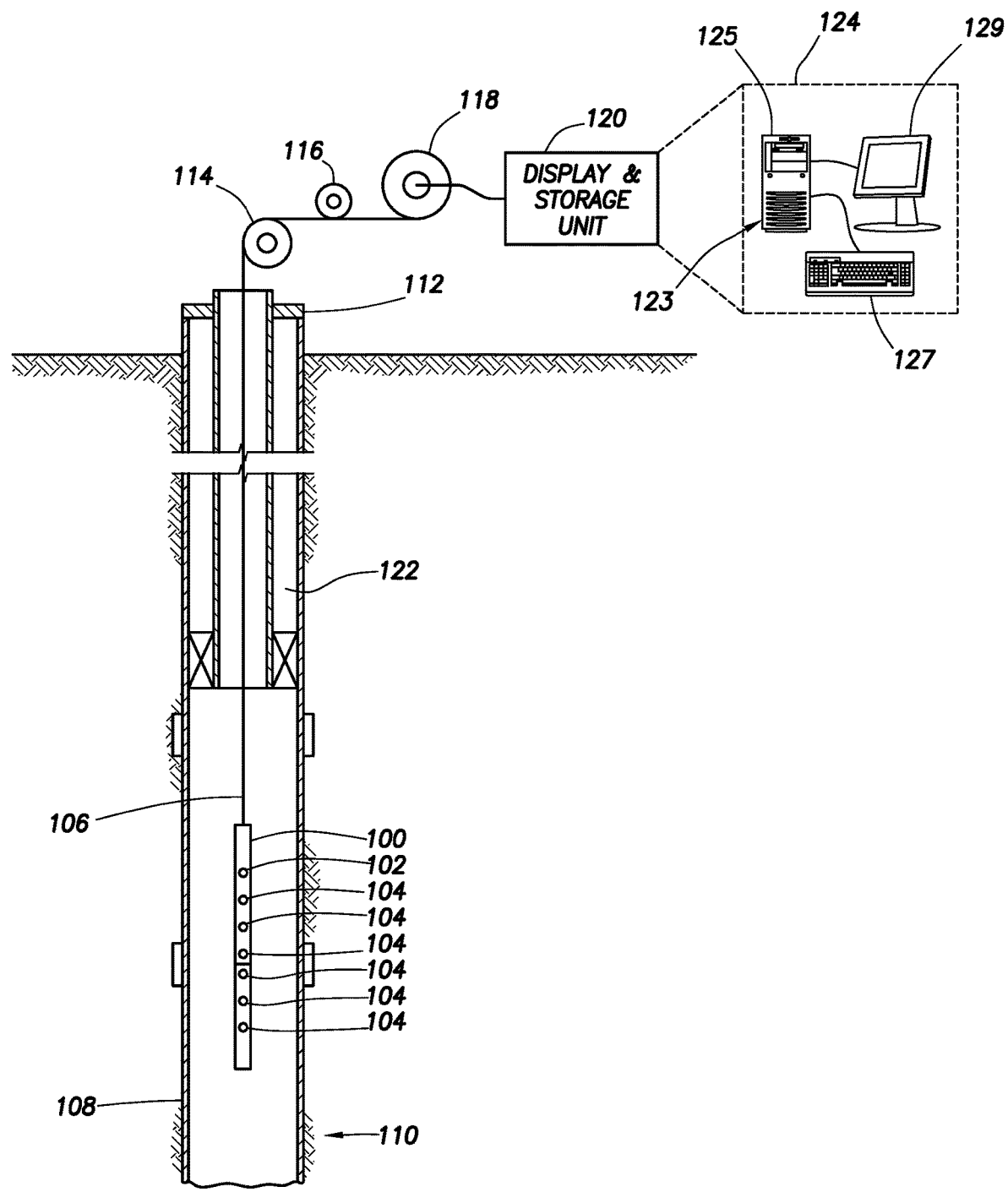
FIG. 1 is a schematic illustration of an operating environment for a defect detection tool.

FIG. 1 illustrates an operating environment for a defect detection tool 100 100 as disclosed herein. Defect detection tool 100 may comprise transmitter 102 and receivers 104. Defect detection tool 100 may be operatively coupled to a conveyance line 106 (e.g., wireline, slickline, coiled tubing, pipe, or the like) which may provide mechanical suspension, as well as electrical connectivity, for defect detection tool 100. Conveyance line 106 and defect detection tool 100 may extend within casing string 108 to a desired depth within the wellbore 110. Conveyance line 106, which may include one or more electrical conductors, may exit wellhead 112, may pass around pulley 114, may engage odometer 116, and may be reeled onto winch 118, which may be employed to raise and lower the tool assembly in the wellbore 110. Signals recorded by defect detection tool 100 may be stored on memory and then processed by display and storage unit 120 after recovery of defect detection tool 100 from wellbore 110. Alternatively, signals recorded by defect detection tool 100 may be conducted to display and storage unit 120 by way of conveyance line 106. Display and storage unit 120 may process the signals, and the information contained therein may be displayed for an operator to observe and stored for future processing and reference. Display and storage unit 120 may also contain an apparatus for supplying control signals and power to the downhole tool assembly, wherein the downhole tool assembly comprises defect detection tool 100.

A typical casing string 108 may extend from wellhead 110 at or above ground level to a selected depth within a wellbore 109. Casing string 108 may comprise a plurality of joints or segments of casing, each segment being connected to the adjacent segments by a threaded collar.

FIG. 1 also illustrates a typical pipe string 122, which may be positioned inside of casing string 108 extending part of the distance down wellbore 110. Pipe string 122 may be production tubing, tubing string, casing string, or other pipe disposed within casing string 108. The defect detection tool 100 may be dimensioned so that it may be lowered into the wellbore 110 through the pipe string 122, thus avoiding the difficulty and expense associated with pulling the pipe string 122 out of the wellbore 110.

In logging systems, such as, for example, logging systems utilizing the defect detection tool 100, a digital telemetry system may be employed, wherein an electrical circuit is used to both supply power to the defect detection tool 100 and to transfer data between display and storage unit 120 and defect detection tool 100. A DC voltage may be provided to the defect detection tool 100 by a power supply located above ground level, and data may be coupled to the DC power conductor by a baseband current pulse system. Alternatively, the defect detection tool 100 may be powered by batteries located within the downhole tool assembly, and/or the data provided by the defect detection tool 100 may be stored within the downhole tool assembly, rather than transmitted to the surface during logging (defect detection). Transmission of electromagnetic fields by the transmitter 102 and the recordation of signals by the receivers 104 may be controlled by an information handling system. Transmitter 102 and receivers 104 may include coils.

Systems and methods of the present disclosure may be implemented, at least in part, with an information handling system 124. As illustrated, the information handling system 124 may be a component of the display and storage unit 120. Alternatively, the information handling system 124 may be a component of defect detection tool 100. An information handling system 124 may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. For example, an information handling system 124 may be a personal computer, a network storage device, or any other suitable device and may vary in size, shape, performance, functionality, and price. The information handling system 124 may include a processing unit 123 (e.g., microprocessor, central processing unit, etc.) that may process data by executing software or instructions obtained from a local or remove non-transitory computer readable media 125 (e.g., optical disks, magnetic disks). The computer readable media 125 may store software or instructions of the methods described herein. Non-transitory computer readable media 125 may include any instrumentality or aggregation of instrumentalities that may retain data and/or instructions for a period of time. Non-transitory computer-readable media 125 may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing The information handling system 124 may also include input device(s) 127 (e.g., keyboard, mouse, touchpad, etc.) and output device(s) 129 (e.g., monitor, printer, etc.). The input device(s) 127 and output device(s) 129 provide a user interface that enables an operator to interact with defect detection tool 100 and/or software executed by processing unit 123. For example, the information handling system 124 may enable an operator to select analysis options, view collected log data, view analysis results, and/or perform other tasks.

Defection detection tool 100 may be used for excitation of transmitters 102. Transmitters 102 may transmit electromagnetic signals into a subterranean formation. The electromagnetic signals may be received and measured by receivers 104 and processed by information handling system 124 to determine pipe parameters, such as, for example, pipe thickness and defected pipes. Non-limiting examples of suitable transmitters 102 may include a coil, a wire antenna, a toroidal antenna, or azimuthal button electrode. As an example, receivers 104 may include receiver coils (e.g., tilted receiver coils), magnetometer receivers, wire antenna, toroidal antenna or azimuthal button electrodes.

Figure 2:
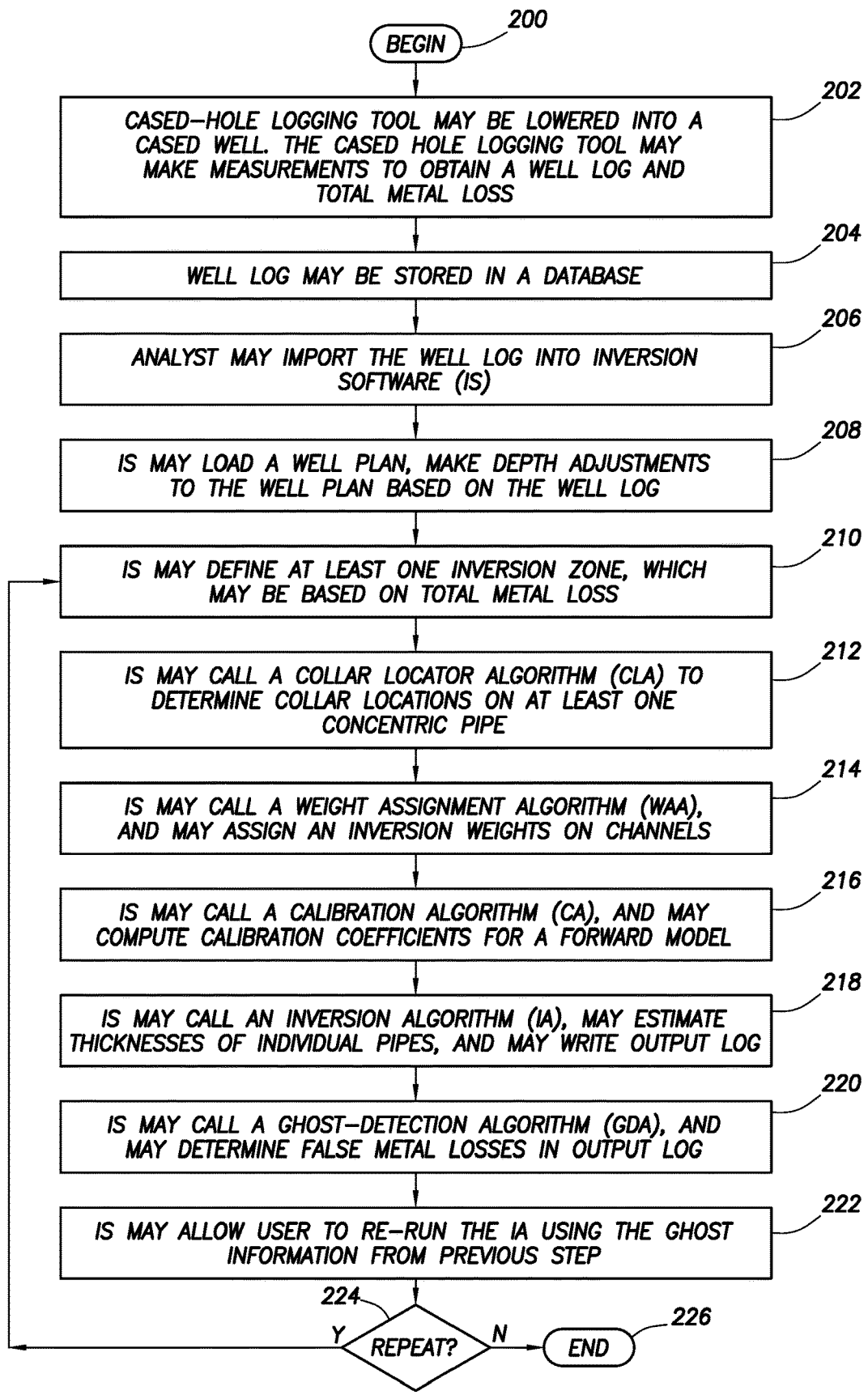
FIG. 2 illustrates an example flow chart of an automated inversion workflow for electromagnetic defect/corrosion inspection.

A workflow in accordance with the present disclosure is shown in FIG. 2. The workflow may begin with box 200. Box 202 provides that a cased-hole logging tool (e.g., defection detection tool 100 on FIG. 1) may be lowered into a cased well (e.g., casing string 108 on FIG. 1). The cased-hole logging tool may make measurements to obtain a well log and total metal loss ("TML"). The well log may comprise induction measurements performed at at least one receiver (e.g., receiver 104 on FIG. 1) and at least one frequency. The excitation may be provided by a transmitter (e.g., transmitter 102 on FIG. 1), placed at a vertical distance from the receiver (e.g., receiver 104 on FIG. 1). The TML measurement may be performed using a remote field eddy current principle. TML may also be obtained by using external tools that measure only the TML.

Figure 3:
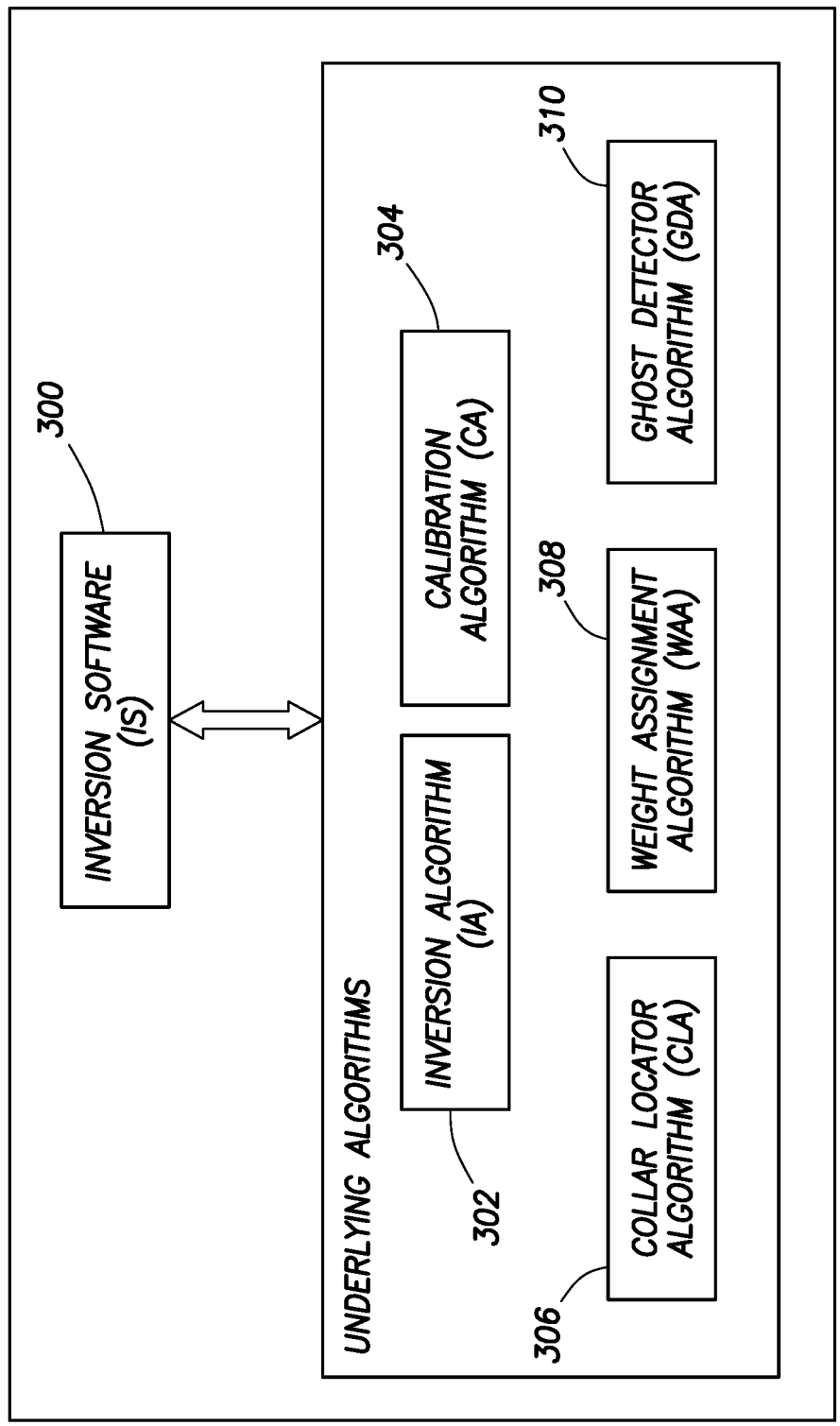
FIG. 3 illustrates underlying algorithms which may be utilized for inversion software.

Box 204 provides that the well log may be stored in a database accessible through a network, or any other suitable form of a data storage medium. The well log may be read by an analyst (either over the network or by obtaining the data storage medium) at a post processing center (e.g., formation evaluation office). Box 206 provides that the analyst may import the well log into the inversion software ("IS"). A schematic description of the IS is shown in FIG. 3. Box 300 provides IS. Box 302 provides an inversion algorithm ("IA"). Box 304 provides a calibration algorithm ("CA"). Box 306 provides a collar locator algorithm ("CLA"). Box 308 provides a weight assignment algorithm ("WAA"). Box 310 provides a ghost detector algorithm ("GDA"). The underlying algorithms called (e.g., utilized) by the IS may be explained in the following steps.

Referring again to FIG. 2, the IS may load the well plan that belongs to the well that has been logged. Box 208 provides that IS may load the well plan, make depth adjustments to the well plan based on the well log. The well plan may show the lengths, start and end depths of all pipes and liners in the completed well. The IS may then compare the well plan and at least one depth-based curve (e.g., a depth-based measurement such as TML) to automatically determine any depth shift that may have occurred during logging. This may be done by comparing at least one major transition point of the well plan and the depth-based curve. Transition points of the depth-based curve may be the curves where a significant change happens in the mean amplitude of the signal. After finding the optimal depth shift, the IS may correct all log curves (e.g., depth-based measurements such as receiver voltages, currents, TML, and other depth-based data) for this depth shift.

Box 210 provides that IS may define at least one inversion zone, which may be based on TML. Inversion zones may be contiguous, non-overlapping log sections where the TML may be above a certain severity threshold. This threshold may depend on the needs of the customer. The default threshold may be set at 5% to 20%, for example. In one particular implementation, the default threshold may be set at 15%.

Box 212 provides that IS may call (e.g., utilize) a CLA to determine collar locations on at least one concentric pipe. The CLA may take collar locations on the innermost pipe from a traditional casing collar locator ("CCL"). The CLA may also determine collar locations on any pipe using more advanced techniques, such as analyzing the periodic sharp signatures of collars on a well log. The final output of the CLA may be a binary (i.e., true or false) collar mask array that may indicate the presence of a collar on any pipe at any depth. The IS may use this mask to optimize the inversion at collar locations (e.g., by allowing more positive thickness changes in the metal). IS may determine updated collar locations on at least one concentric pipe in the wellbore utilizing the collar locator algorithm in the inversion software using the well log, well plan and the output log. Additionally, IS may generate an updated output log using the updated collar locations, may determine updated false metal loss in the output log using the output log, well plan and updated collar locations and may generate an updated output log using the false metal loss.

Figure 4:
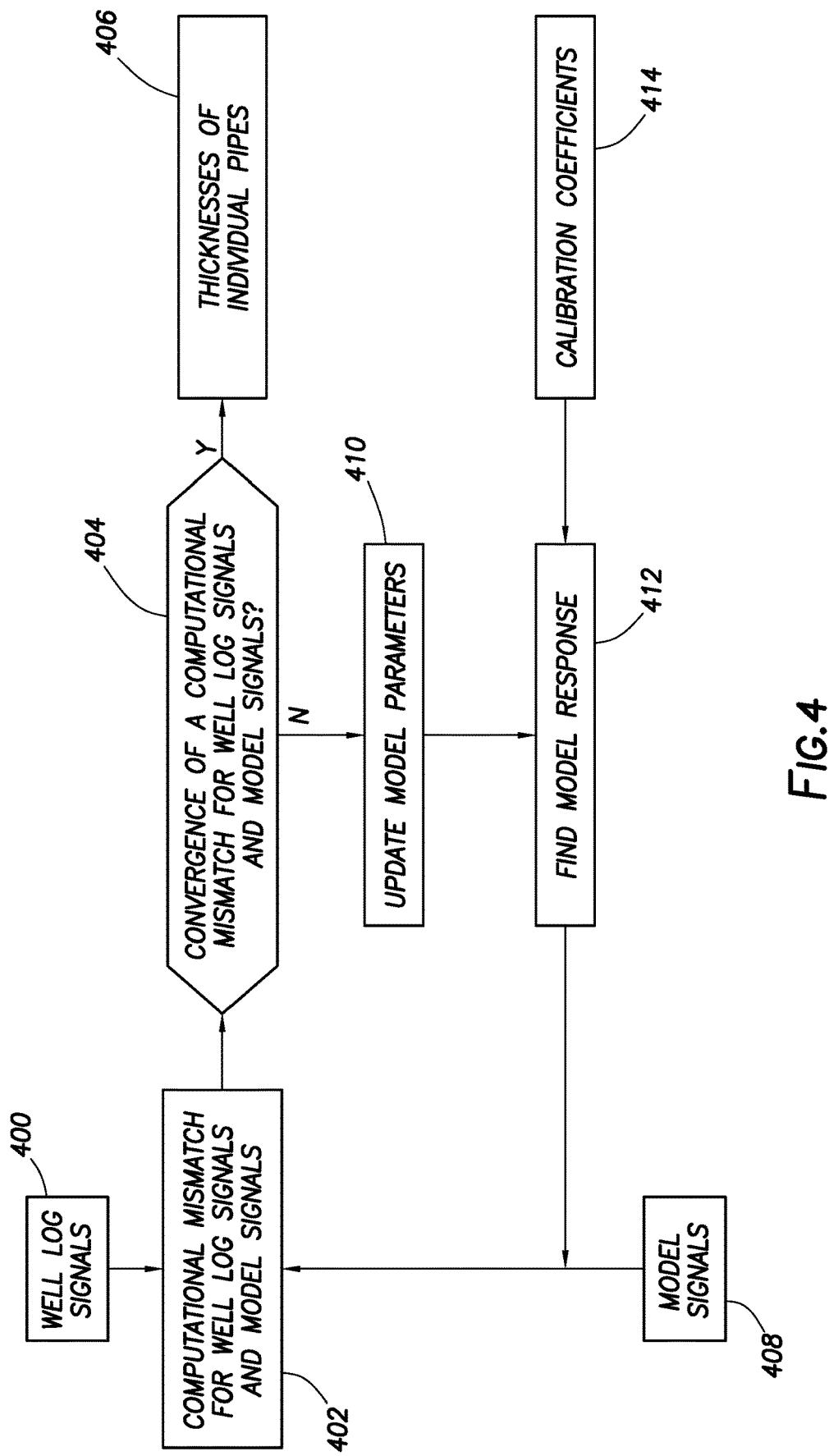
FIG. 4 illustrates an example flow chart of an inversion algorithm.

Box 214 provides that the IS may call a WAA that automatically assigns weights to each channel (i.e. receiver/frequency combination) in the cost function associated with the inversion algorithm, as shown in FIG. 4. Box 400 provides well log signals. Box 402 provides a computational mismatch for the well log signals and the model signals. Box 404 provides whether there is a convergence for the computational mismatch of the well log signals and the model signals. Box 406 provides thicknesses of individual pipes. Box 408 provides model signals. Box 410 provides updating model parameters. Box 412 provides finding a model response. Box 414 provides calibrating coefficients. Different inversion zones may get different weight assignments, since the number of concentric casings may be different in each zone. The weight values may be determined by previous research on the underlying inversion algorithm. Two aspects of the inversion algorithm may include: (1) The sensitivity of each channel to the model parameters (i.e. metal thicknesses on each pipe), (2) possible detrimental factors, such as noise, model inaccuracy, and measurement inaccuracy. The WAA may assign equal weight to all of the channels.

Referring again to FIG. 2, box 216 provides that IS may call a CA and may compute calibration coefficients for a forward model. The CA is run separately inside each inversion zone. There may be a single calibration done for the entire zone, or multiple calibrations inside sub-zones of smaller lengths defined by a user of the IS. The CA may statistically analyze a well log in the inversion zone (or sub-zone), and may find a nominal zone where the pipes were not corroded and otherwise defect-free. These zones may be statistically common in a well log, since defects may be an exception, rather than a rule in any given well. The ratios between the measured voltages in a nominal zone and the simulated voltages from a forward model may be calibration coefficients, which may be applied to a forward model in subsequent inversion runs.

Box 218 provides that IS may call an IA which may estimate thicknesses of individual pipes and may write the estimated thicknesses to an output log. The IS may call an IA on each inversion zone. The IA may start with an initial guess for model parameters (i.e., metal thicknesses for each pipe), and may update these parameters using an optimization algorithm (e.g., Gauss-Newton, Levenberg-Marquardt) until a cost function is minimized. The cost function may be an absolute-square difference between a well log and a calibrated forward model result. The IS may display estimated metal thicknesses for each pipe to a user as an output log.

Box 220 provides that IS may call a GDA that may determine false metal losses in an output log. The IS may call a GDA that automatically determines ghosts, which are false metal losses that appear as sharp, periodic peaks in the output log. These apparent losses may actually be a consequence of collars; or more specifically, the inability of the inversion algorithm to fully account for their presence due to a finite vertical resolution of the defect detection tool 100. Many defect detection tools have a vertical resolution of several feet, while the largest collars may have a vertical resolution of about a foot. The GDA may detect ghosts in an output log automatically in the same way the CLA detects collar signatures in a well log (i.e., by exploiting a periodicity of ghost signatures). A final output of the GDA may be a binary ghost mask array that indicates a presence of a ghost (e.g., true or false) on any pipe at any depth.

Box 222 provides that IS may allow a user to re-run an IA using the ghost information from the previous step (e.g., Box 220). The IS may present to a user (e.g., via a monitor), an option to re-run an inversion (e.g., starting from Box 218) using the ghost mask array as an inversion constraint. The inversion constraint may be that the metal losses be assigned zero at locations where the ghost mask is equal to 1, in order to remove sharp peaks in the output log. For efficiency, the inversion algorithm may be re-run only at locations where the ghost mask is 1, and the original results may be kept the same. The IS may present updated results to a user. Box 224 provides that Box 210 through Box 220 may be repeated, as necessary. Box 226 provides the end of the workflow.

The systems and methods may include any of the various features of the systems and methods disclosed herein, including one or more of the following statements.

Statement 1: A defect detection method comprising: disposing a defect detection tool in a wellbore, wherein the defect detection tool comprises a transmitter and a plurality of receivers; processing measurements from the defect detection tool in the wellbore to obtain a well log, wherein the well log comprises a metal loss measurement; storing the well log in a database; importing the well log from the database into inversion software; loading a well plan into the inversion software; determining collar locations on at least one concentric pipe in the wellbore utilizing a collar locator algorithm in the inversion software using the well log and well plan; calibrating a forward model in the inversion algorithm utilizing a calibration algorithm in the inversion software using well log, well plan and collar locations; generating an output log utilizing the inversion algorithm in the inversion software on the inversion zone, wherein the output log comprises metal thicknesses of at least one concentric pipe of a plurality of concentric pipes, and collar locations; and determining false metal loss in the output log using the output log, well plan and collar locations.

Statement 2: The defect detection method of statement 1, further comprising determining updated collar locations on at least one concentric pipe in the wellbore utilizing the collar locator algorithm in the inversion software using the well log, well plan and the output log.

Statement 3: The defect detection method of statement 2, further comprising generating an updated output log using the updated collar locations.

Statement 4: The defect detection method of any preceding statement, further comprising determining updated false metal loss in the output log using the output log, well plan and updated collar locations.

Statement 5: The defect detection method of any preceding statement, further comprising generating an updated output log using the false metal loss.

Statement 6: The defect detection method of any preceding statement, further comprising comparing the well plan to depth-based measurements on the well log to determine a depth shift.

Statement 7: The defect detection method of statement 6, further comprising correcting the depth-based measurements for the depth shift.

Statement 8: The defect detection method of any preceding statement, further comprising defining at least one inversion zone, wherein the inversion zone is a contiguous non-overlapping section of the well log where metal loss is above a threshold.

Statement 9: The defect detection statement 8 of claim 8, wherein the threshold ranges from 5% to 20%.

Statement 10: The defect detection method of any preceding statement, further comprising assigning weights to a channel in a cost function of an inversion algorithm utilizing a weight assignment algorithm in the inversion software, wherein the channel comprises receiver and frequency combinations.

Statement 11: The defect detection method of any preceding statement, further comprising analyzing periodic signatures of collars on the well log to determine collar locations and outputting a binary collar mask array.

Statement 12: The defect detection method of statement 11, wherein the binary collar mask array comprises an indication of a presence of a collar on a pipe at a depth.

Statement 13: The defect detection method of statement 12, further comprising optimizing an inversion at collar locations with the binary collar mask array.

Statement 14: A defect detection system comprising: a defect detection tool, wherein the defect detection tool comprises a transmitter and a plurality of receivers; and an information handling system in communication with the defect detection tool, wherein the information handling system is configured to: process measurements from the defect detection tool in the wellbore to obtain a well log, wherein the well log comprises a metal loss measurement; store the well log in a database; import the well log from the database into inversion software; load a well plan into the inversion software; determine collar locations on at least one concentric pipe in the wellbore utilizing a collar locator algorithm in the inversion software using the well log and well plan; calibrate a forward model in the inversion algorithm utilizing a calibration algorithm in the inversion software using well log, well plan and collar locations; generate an output log utilizing the inversion algorithm in the inversion software on the inversion zone, wherein the output log comprises metal thicknesses of at least one concentric pipe of a plurality of concentric pipes, and collar locations; and determine false metal loss in the output log using the output log, well plan and collar locations.

Statement 15: The defect detection system of statement 14, wherein the information handling system is further configured to determine updated collar locations on at least one concentric pipe in the wellbore utilizing the collar locator algorithm in the inversion software using the well log, well plan and the output log.

Statement 16: The defect detection system of statement 15, wherein the information handling system is further configured to generate an updated output log using the updated collar locations.

Statement 17: The defect detection system of any one of statements 14 to 16, wherein the information handling system is further configured to determine updated false metal loss in the output log using the output log, well plan and updated collar locations.

Statement 18: The defect detection system of statement 17, wherein the information handling system is further configured to generate an updated output log using the false metal loss.

Statement 19: The defect detection system of any one of statements 14 to 18, wherein the information handling system is further configured to compare the well plan to depth-based measurements on the well log to determine a depth shift.

Statement 20: The defect detection system of statement 19, wherein the information handling system is further configured to correct the depth-based measurements for the depth shift.

The preceding description provides various examples of the systems and methods of use disclosed herein which may contain different method steps and alternative combinations of components. It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only, and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A defect detection method comprising:
    disposing a defect detection tool in a wellbore, wherein the defect detection tool comprises a transmitter and a plurality of receivers;
    processing measurements from the defect detection tool in the wellbore to obtain a well log, wherein the well log comprises a metal loss measurement;
    storing the well log in a database;
    importing the well log from the database into inversion software;
    loading a well plan into the inversion software;
    determining collar locations on at least one concentric pipe in the wellbore utilizing a collar locator algorithm in the inversion software using the well log and well plan;
    calibrating a forward model in the inversion algorithm utilizing a calibration algorithm in the inversion software using well log, well plan and collar locations;
    generating an output log utilizing the inversion algorithm in the inversion software on the inversion zone, wherein the output log comprises metal thicknesses of at least one concentric pipe of a plurality of concentric pipes, and collar locations;
    determining one or more updated collar locations on at least one concentric pipe in the wellbore utilizing the collar locator algorithm in the inversion software using the well log, well plan and the output log; and
    determining false metal loss in the output log using the output log, well plan and collar locations.

2. The defect detection method of claim 1, further comprising generating an updated output log using the updated collar locations.

3. The defect detection method of claim 1, further comprising determining updated false metal loss in the output log using the output log, well plan and the one or more updated collar locations.

4. The defect detection method of claim 3, further comprising generating an updated output log using the false metal loss.

5. The defect detection method of claim 1, further comprising comparing the well plan to depth-based measurements on the well log to determine a depth shift.

6. The defect detection method of claim 5, further comprising correcting the depth-based measurements for the depth shift.

7. The defect detection method of claim 1, further comprising defining at least one inversion zone, wherein the inversion zone is a contiguous non-overlapping section of the well log where metal loss is above a threshold.

8. The defect detection method of claim 7, wherein the threshold ranges from 5% to 20%.

9. The defect detection method of claim 1, further comprising assigning weights to a channel in a cost function of an inversion algorithm utilizing a weight assignment algorithm in the inversion software, wherein the channel comprises receiver and frequency combinations.

10. The defect detection method of claim 1, further comprising analyzing periodic signatures of collars on the well log to determine collar locations and outputting a binary collar mask array.

11. The defect detection method of claim 10, wherein the binary collar mask array comprises an indication of a presence of a collar on a pipe at a depth.

12. The defect detection method of claim 11, further comprising optimizing an inversion at collar locations with the binary collar mask array.

13. A defect detection system comprising:
    a defect detection tool, wherein the defect detection tool comprises a transmitter and a plurality of receivers; and
    an information handling system in communication with the defect detection tool, wherein the information handling system is configured to:
        process measurements from the defect detection tool in the well bore to obtain a well log, wherein the well log comprises a metal loss measurement;
        store the well log in a database;
        import the well log from the database into inversion software;
        load a well plan into the inversion software;
        determine collar locations on at least one concentric pipe in the wellbore utilizing a collar locator algorithm in the inversion software using the well log and well plan;
        calibrate a forward model in the inversion algorithm utilizing a calibration algorithm in the inversion software using well log, well plan and collar locations;
        generate an output log utilizing the inversion algorithm in the inversion software on the inversion zone, wherein the output log comprises metal thicknesses of at least one concentric pipe of a plurality of concentric pipes, and collar locations;
        determine one or more updated collar locations on at least one concentric pipe in the wellbore utilizing the collar locator algorithm in the inversion software using the well log, well plan and the output log; and
        determine false metal loss in the output log using the output log, well plan and collar locations.

14. The defect detection system of claim 13, wherein the information handling system is further configured to generate an updated output log using the updated collar locations.

15. The defect detection system of claim 13, wherein the information handling system is further configured to determine updated false metal loss in the output log using the output log, well plan and the one or more updated collar locations.

16. The defect detection system of claim 15, wherein the information handling system is further configured to generate an updated output log using the false metal loss.

17. The defect detection system of claim 13, wherein the information handling system is further configured to compare the well plan to depth-based measurements on the well log to determine a depth shift.

18. The defect detection system of claim 17, wherein the information handling system is further configured to correct the depth-based measurements for the depth shift.

* * * * *